United States Patent [19]

Turner et al.

[11] 4,338,097
[45] Jul. 6, 1982

[54] CORROSION MONITORING PROCESS AND APPARATUS FOR USE THEREIN

[75] Inventors: Mervyn E. D. Turner, Middlesbrough; Joshua C. Quayle, Stockton-on-Tees, both of England

[73] Assignee: Imperial Chemical Industries Limited, London, England

[21] Appl. No.: 217,151

[22] Filed: Dec. 16, 1980

[30] Foreign Application Priority Data

May 8, 1980 [GB] United Kingdom ............... 8015221

[51] Int. Cl.³ ............................................. G01N 17/00
[52] U.S. Cl. ................................. 23/230 C; 116/208; 422/53
[58] Field of Search ................. 23/230 C; 422/53; 116/208; 73/86

[56] References Cited

U.S. PATENT DOCUMENTS

| | | | |
|---|---|---|---|
| 2,856,495 | 10/1958 | Chittum et al. | 338/10 |
| 3,085,426 | 4/1963 | Freedman | 73/86 |
| 3,094,865 | 6/1963 | Dravnieks | 73/86 |
| 3,504,323 | 3/1970 | Meany, Jr. | 338/13 |
| 4,267,148 | 5/1981 | Dickson et al. | 23/230 C |

OTHER PUBLICATIONS

"Corrosion" 14 Mar. 1958, pp. 55-58.
"IEC" 52 Oct. 1960, pp. 67A, 68A & 70A.

*Primary Examiner*—Ronald E. Serwin
*Attorney, Agent, or Firm*—Cushman, Darby & Cushman

[57] ABSTRACT

Corrosion of a component surface, e.g. the surface of a pipe, is monitored by monitoring the thickness, e.g. by resistance measurement, of a test element formed from the material of the component and mounted so that its exposed surface is flush with and extends over substantially all of one dimension of the component surface, e.g. substantially all round the circumference of a pipe.

12 Claims, 6 Drawing Figures

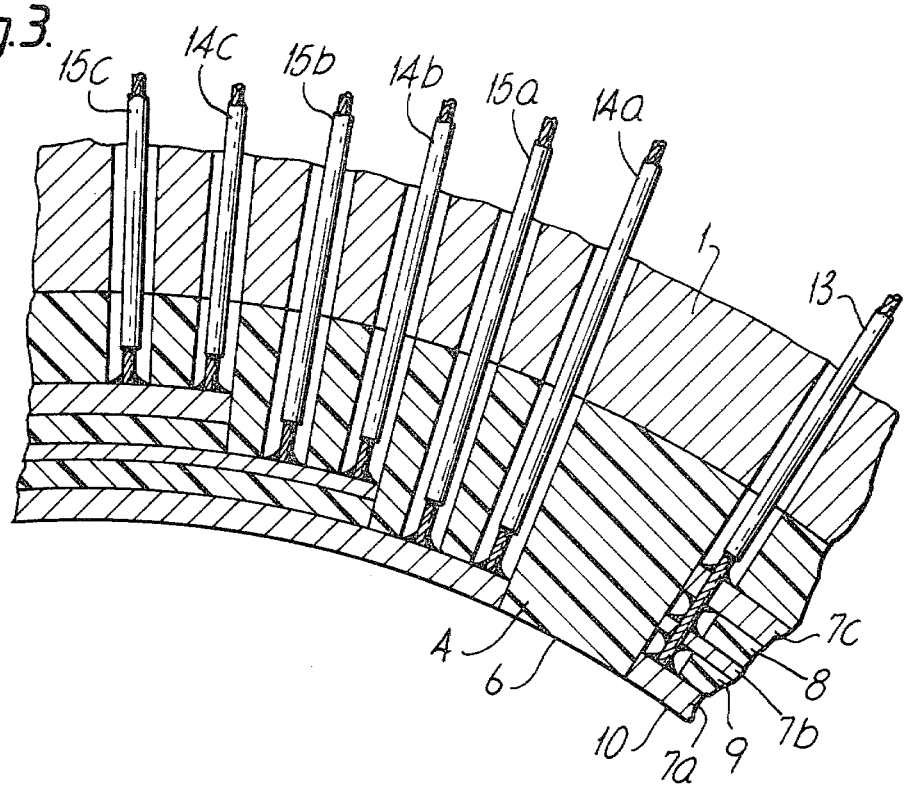
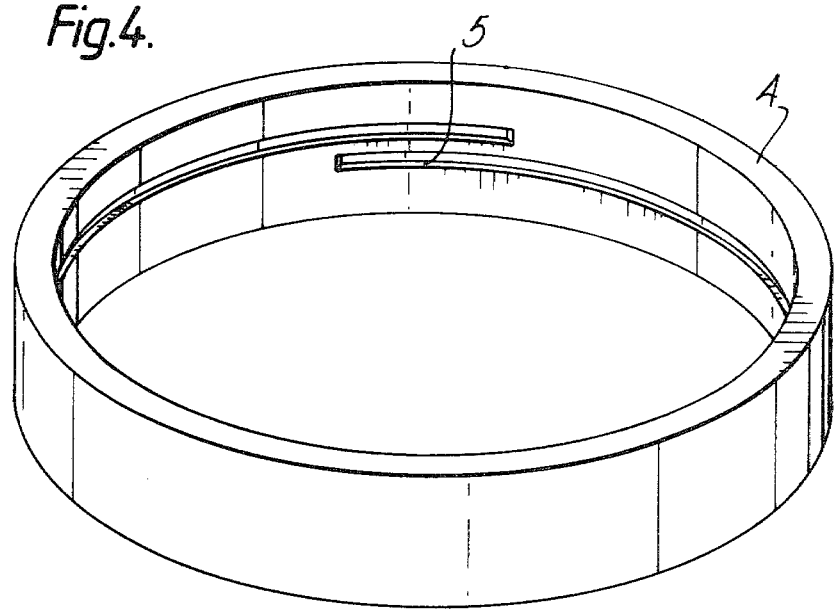

CORROSION MONITORING PROCESS AND APPARATUS FOR USE THEREIN

This invention relates to corrosion monitoring and in particular to a corrosion monitoring process, and to apparatus for use therein, and to certain component parts of the apparatus.

It is often desirable to monitor corrosion of the surface of certain components, particularly fluid containment devices such as pipes or vessels, so that warning can be given of when the component requires replacement or maintenance. When the surface of the component subject to corrosion by its environment, e.g. by a fluid flowing through a pipe, is electrically conductive, the rate of corrosion can be monitored by monitoring the change in electrical resistance of a test element subjected to the same environment as that to which the component is subject. Corrosion causes a reduction in thickness of the element with a consequential increase in indicated resistance.

In one form of corrosion monitoring device that has been widely used, a test element in the form of a wire or ribbon drawn or rolled from the same material as the component is mounted in a housing or probe projecting through the component surface. This type of arrangement suffers from a number of disadvantages, inter alia, (a) It is not always possible to draw the material of the component into a wire or ribbon and so cannot be used for some materials.

(b) to get adequate sensitivity to corrosion, the element must be made very thin: this means that it is liable to have a short life and also is liable to mechanical damage, particularly where it is used in a pipe that it is desired to "pig" periodically.

(c) the projecting probe and element is subject to environmental conditions at points away from the component surface and so may not reflect the effect of conditions at the surface. Also such a projecting probe may cause turbulence with associated different corrosion effects.

In an attempt to overcome some of these disadvantages, another form of probe has been used in some cases. In this form the probe is arranged so that the element is a short length of material flush with the component surface. Again, because of its short length, the element is necessarily thin to obtain adequate sensitivity and hence has a short life. Also it is difficult to ensure that the element is actually flush with the component surface. A further disadvantage is that the probe only monitors the corrosion at one point on the pipe or vessel periphery whereas corrosion may proceed at different rates at different locations, e.g. at different locations around the circumference of a pipe cross-section.

In the present invention these disadvantages are overcome by using a test element extending over substantially all of one dimension of the component surface; e.g. where the surface is the interior surface of a pipe, the test element extends round all, or nearly all, the pipe interior cross-section, and so may have a much longer length than with prior probe designs, and hence a considerably longer life can be achieved without sacrifice of sensitivity. The test element surface is mounted flush with the component surface and can be machined from the component itself (or from a spare identical component) and so can reflect the metallurgical structure of the component.

Accordingly we provide a method of monitoring corrosion of the surface of a component subject to a corrosive environment comprising (a) forming an elongated strip test element from the material of said component, (b) mounting said element so that one surface thereof is flush with said component surface, is exposed to said corrosive environment, and extends over at least substantially all of one dimension of said component surface, and (c) monitoring the thickness of said element.

We also provide a probe for use in monitoring corrosion of the surface of a component subject to a corrosive environment comprising (a) a housing adapted to be connected in-line with said component with its surface exposed to the corrosive environment flush with said surface of the component and (b) an elongated strip test element formed from the material of said component mounted in said housing with one surface of said element flush with said surface of the housing, exposed to the corrosive environment, and extending over substantially all of one dimension of said component surface.

We further provide apparatus for use in monitoring corrosion of the surface of a component subject to a corrosive environment comprising a probe as aforesaid in combination with means to monitor the thickness of said element.

The thickness of the test element may be monitored by any suitable method, e.g. by ultrasonics, vibrational frequency measurement, and induction impedance measurement in which case an element in the form of a complete ring may be employed. However where the test element is of an electrically conducting material, the thickness is preferably monitored by measurement of its electrical resistance. In this case the test element is mounted so that it is electrically insulated from the component, except possibly at one point.

Because variations in the environmental temperature may cause greater changes in the parameter, e.g. resistance, used to monitor thickness than those changes caused by corrosion, the thickness of the test element is preferably compared with that of a similar element, hereinafter termed the reference element, mounted adjacent to the test element. The reference element is protected from corrosion but is subject to the same temperature variations as the test element.

BRIEF DESCRIPTION OF THE DRAWINGS

The invention is illustrated by reference to the accompanying drawings wherein:

FIG. 3 is a section along line III—III of FIG. 2, FIG. 4 is an isometric view of an alternative form of liner for the element housing.

In FIG. 1 the invention is shown applied to the monitoring of corrosion on the interior surface of a mild steel pipe by a resistance measuring technique. The monitoring probe comprises an annular housing 1 formed from mild steel bolted between adjacent flanges 2a, 2b of adjacent lengths 3a, 3b of the pipe. Housing 1, which has an internal diameter equal to that of the pipe, has a flush inner liner 4 formed from an electrically insulating material such as polytetrafluoroethylene. The liner has a recess, or groove, 5 extending round its interior cylindrical surface 6 in which are located three strip elements 7 formed from thin rings of about 5 mm width machined from the interior surface of a sample length of the pipe. Since the rings are machined from a sample of the pipe they reflect not only the chemical composition thereof, but also its metalurgical structure.

Figure 1:
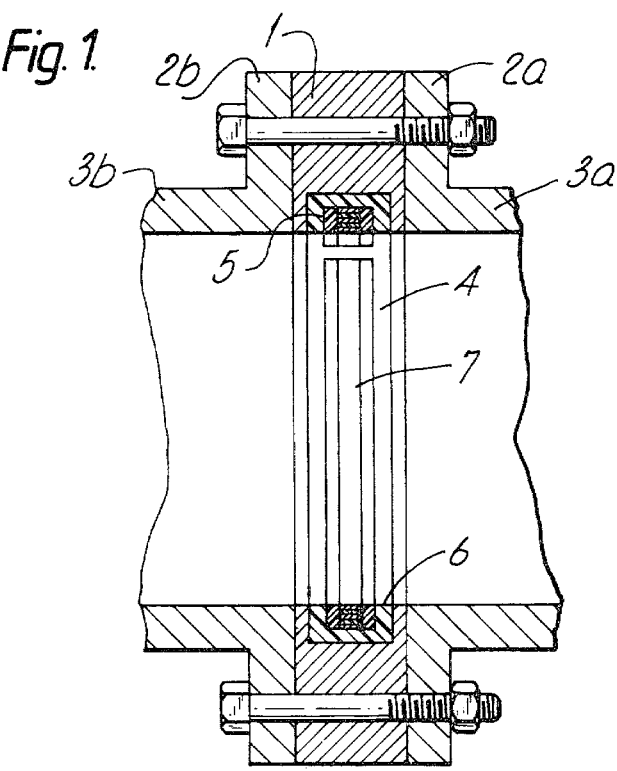
FIG. 1 is a longitudinal section through a pipe having a corrosion monitoring device mounted in line therewith.
Figure 2:
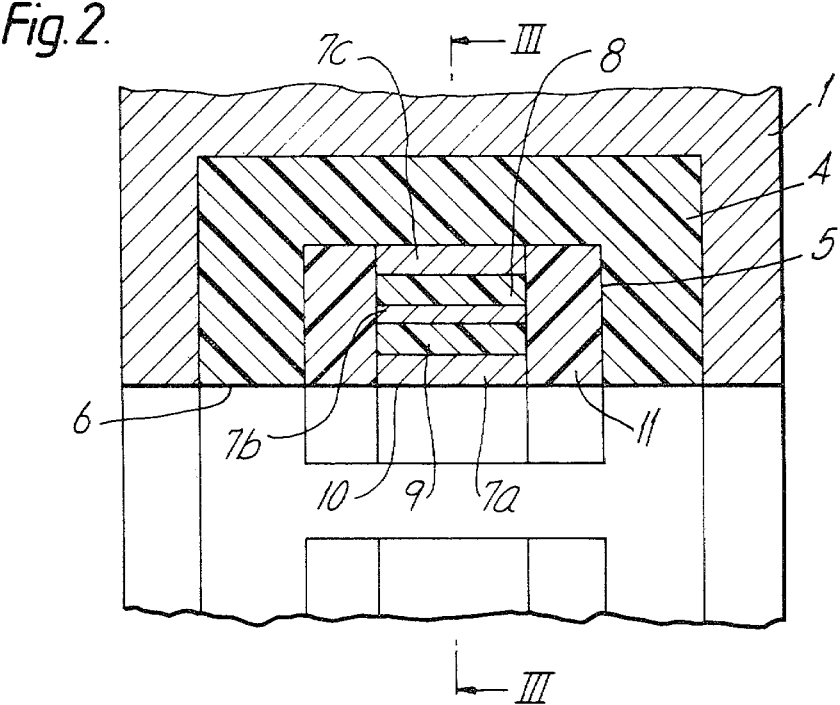
FIG. 2 is an enlarged section of part of the element housing.

The assembly of the elements in groove 5 is shown enlarged in FIGS. 2 and 3. At the bottom of the groove 5 is located a check element 7c, and, after interposing a layer 8 of an insulant, e.g. fibre glass, the reference element 7b is inserted. A further layer 9 of insulant is applied and then the test element 7a is inserted so that the inner face 10 of element 7a is flush with the surface 6 of the liner 4 which in turn is flush with the interior surface of pipes 3a, 3b. The sides of the groove 5 are filled with a suitable insulant sealer 11 such as an epoxy resin so as to hold the elements in position and to protect all the surfaces thereof, except surface 10 of element 7a, from corrosion. As a further protection against corrosion all the surfaces of the elements, except surface 10 of element 7a, may be given a protective coating prior to insertion of the elements into groove 5.

Element 7a, the test element, and element 7c, a check element, have thicknesses of about 1–2 mm while element 7b, the reference element, may be thinner, e.g. 0.5–1 mm. The cross-sectional dimensions of the elements should be very small in comparison to their length. As shown in FIG. 3, holes 12 are provided through the housing wall and liner whereby insulated electrical leads are passed and soldered, or otherwise fastened, to the elements. In the circuit arrangement described hereinafter, test element 7a is to be connected in series with the reference element 7b and in parallel with check element 7c. To this end one lead 13 is connected to one end of all the elements while two leads 14, 15 are connected to the free, i.e. other ends of each of the elements.

It will be appreciated that, depending on the circuitry employed for resistance measurement, it may be necessary to have each element isolated from the others with no common connection. In that case, separate leads are required for each end of the elements. In other arrangements it may be desired to connect all of the elements in series in which case one lead should be connected to one end of two of the elements, another lead connected to the other end of one of the elements and to one end of the third element and two leads connected to each of the free element ends.

It will further be appreciated that the liner 4 could be omitted and the recess or groove 5 formed in a housing made from an electrically conductive material: in this case the elements should be insulated from each other and from the housing, although, where the resistance measurement circuitry permits, the elements could be electrically connected to the housing at one point: e.g. a common connection to one end of all three elements could be made by the housing itself. Where an insulating liner is employed, the electrical connections could be made via studs extending through the liner instead of via leads soldered or otherwise fastened to the elements themselves.

The test element 7a extends almost completely round the interior wall of the pipe and so will monitor corrosion occuring anywhere round the pipe wall. If desired, the groove 5 may be made as a helix with overlapping ends, as shown in FIG. 4, to ensure monitoring of the complete pipe cross-section. Indeed, to obtain greater sensitivity by means of a lengthened test element, the groove 5, and also the elements 7, may be in the form of helices having more than one turn.

Element 7a is the test element and has its resistance compared, e.g. by means described hereinafter, with that of the reference element 7b. The purpose of the check element 7c is to indicate, by comparison of its resistance with that of the reference element 7b, whether an "open-circuit" indication is a result of such complete corrosion of test element 7a that the latter breaks and hence gives an open-circuit indication or is a result of a fault in the resistance measurement circuitry: thus if check element 7c gives an open circuit indication, then a fault in the circuitry is indicated.

In some cases check element 7c may be omitted as periodic monitoring will indicate the increase of resistance of element 7a, and hence its corrosion.

Figure 5:
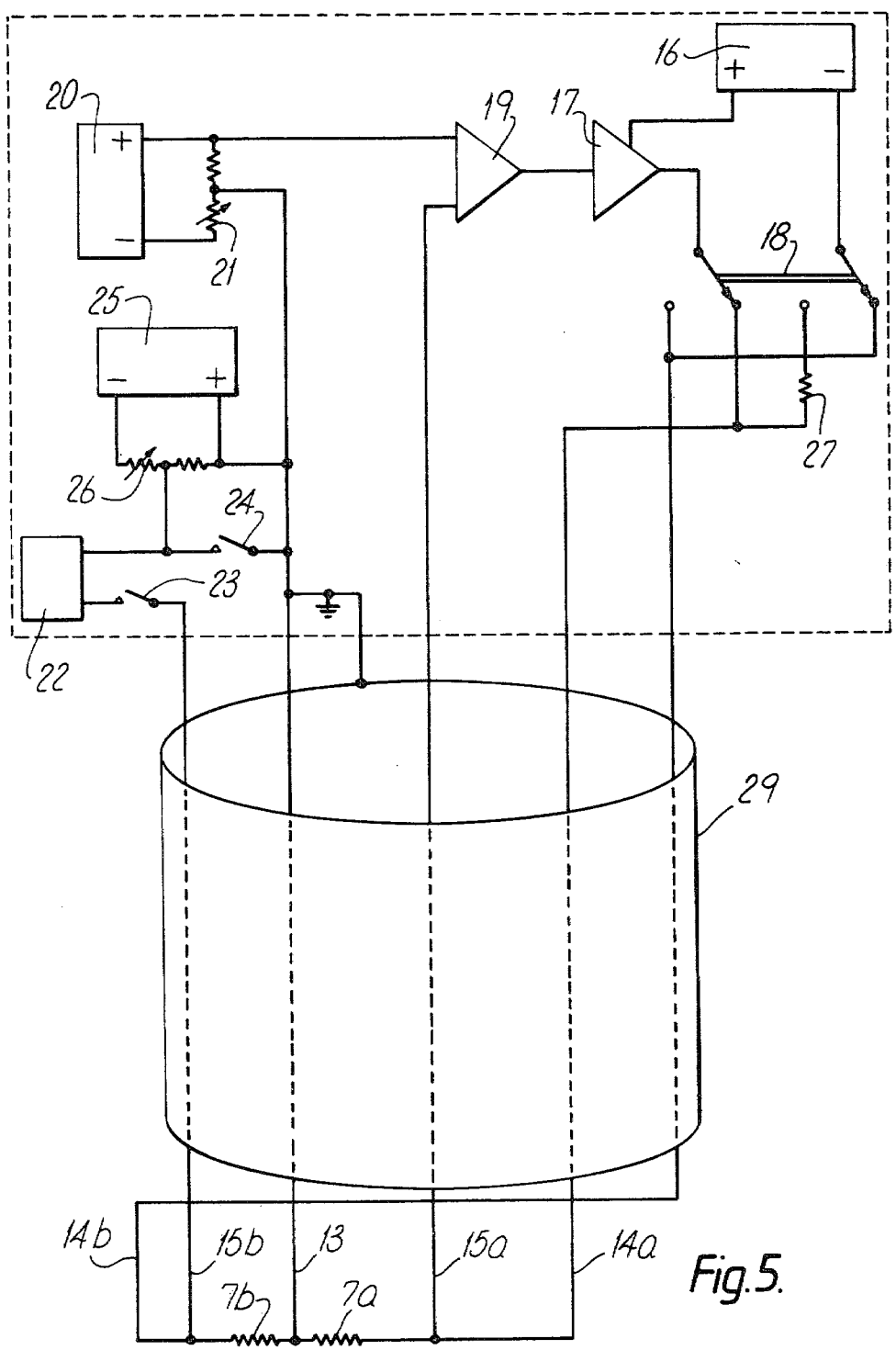
FIG. 5 is a circuit diagram for monitoring the thickness change by resistance measurement.
Figure 6:
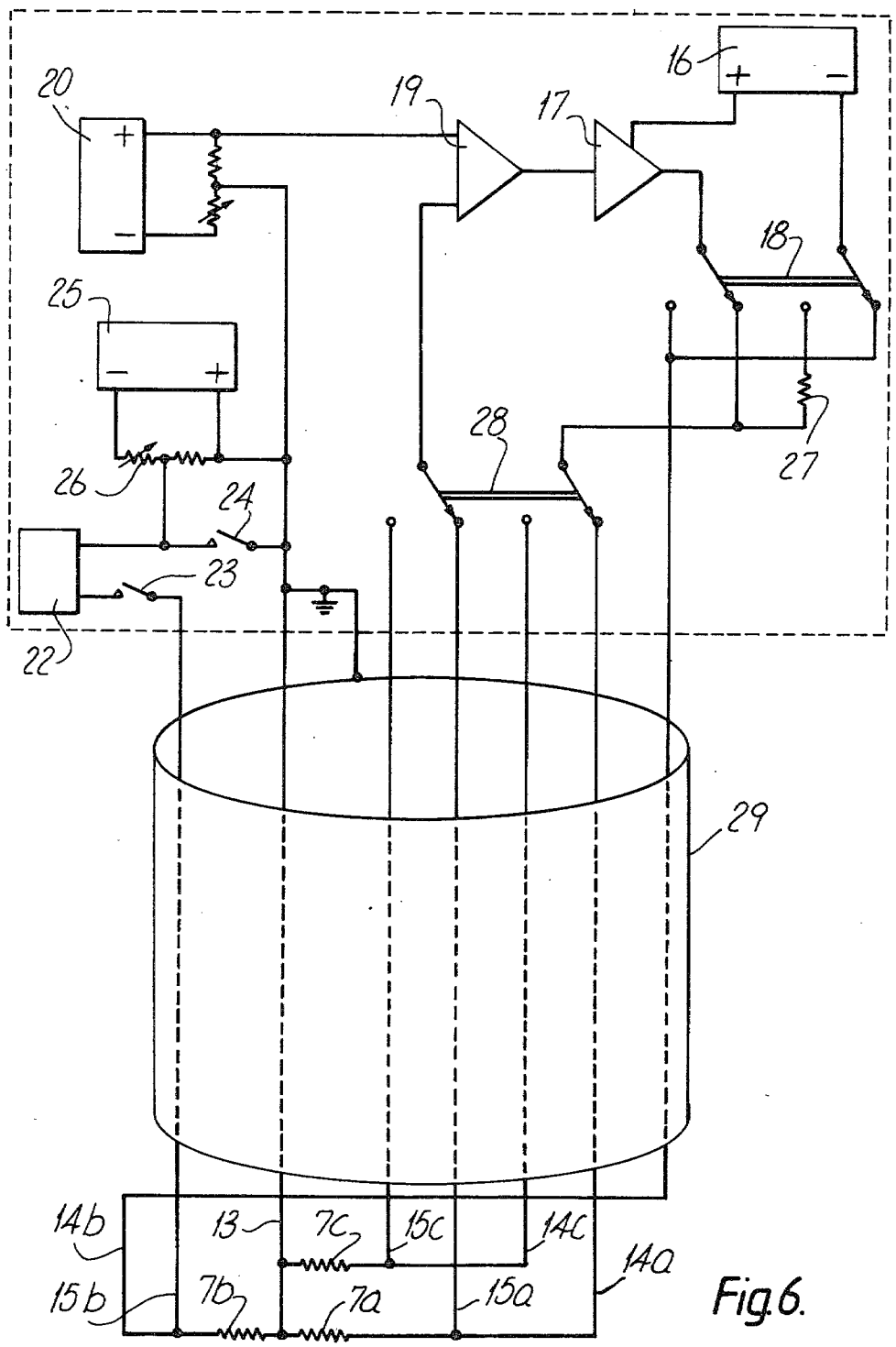
FIG. 6 is part of the circuit diagram of FIG. 5 showing a modification thereto for use where a check element is employed.

A suitable resistance comparing circuit for a system in which no check element is used is shown in FIG. 5 while FIG. 6 illustrates the modification thereto for use where a check element is employed.

In FIG. 5, the circuit comprises a direct current power supply 16 which feeds a current i through the test element 7a and reference element 7b connected in series, via a solid state, integrated circuit, current amplifier 17 and a reversing switch 18, through leads 14a, 14b. The voltage drop Va, typically arranged to be about 20 mV, across element 7a is fed back to a solid state, integrated circuit, voltage comparator 19, via leads 13 and 15a, where it is compared with a standard voltage, e.g. 20 mV, obtained from a voltage standard 20 feeding a potential divider having an adjustable resistance 21 by means of which the standard voltage can be preset. The output from the voltage comparator 19 controls the current amplifier 17 to modify the current i flowing through elements 7a, 7b to maintain the voltage drop Va across element 7a constant and equal to the preset standard voltage.

The voltage drop Vb across the reference element 7b can be measured by a voltmeter, e.g. a digital voltmeter, 22 connected to leads 13 and 15b via on-off switches 23 and 24. The voltage drop Vb across the reference element 7b is typically about 40 mV—if the thickness of element 7b is half that of element 7a, the voltage drop Vb across element 7b will be about twice that of the voltage drop Va across element 7a if the elements are of similar width and length.

Switch 23 is only closed when a measurement is to be taken. When switch 24 is open a biasing voltage is applied to the voltmeter 22. This biasing voltage is obtained from a voltage standard 25 feeding a potential divider having an adjustable resistance 26 by means of which the biasing voltage can be preset. If the bias voltage is made equal to the voltage drop Vb across the protected element 7b the net voltage registered by the voltmeter 22 is zero.

Since the resistance R of an element 7 is inversely proportional to its thickness t $$\frac{Rb}{Ra} = \frac{ta}{tb}$$

-continued and so $$\frac{Vb}{Va} = \frac{ta}{tb}$$

Therefore $$Vb = \frac{Va}{tb} \cdot ta$$

Hence the voltage drop Vb across the protected element 7b is directly proportional to the thickness of the test element 7a, and so, as the test element 7a corrodes, the voltage drop Vb across the protected element 7b decreases.

By making the bias voltage equal to Vb when the test element 7a is in the original uncorroded state, the voltage indicated by the voltmeter 22 is directly proportional to the decrease in thickness. The voltmeter can therefore be calibrated in terms of thickness lost by corrosion. When switch 24 is closed, the bias voltage is shorted out so that the voltage indicated by the voltmeter 22 is directly proportional to the thickness of the test element 7a.

The purpose of the reversing switch 18 is so that the current flowing through the test element can periodically be reversed in polarity hence avoiding cathodic protection of one end of the test element 7a. Conveniently reversing switch 18 is driven at half the mains frequency i.e. 25 Hz by means not shown.

When a measurement is to be taken by closing switch 23, the reversing switch 18 must be held in the position shown in FIG. 5. When switch 18 is in the other position, the polarity of the feed back voltage to voltage comparator 19 is reversed thus driving the output thereof to saturation thus tending to drive the current amplifier 17 to saturation. To limit the current i when the polarity is in this reversed state, a resistance 27 is provided in series with the test and reference elements 7a, 7b.

It will be appreciated that, by insertion of a precision rectifying system in the lead 15a to voltage comparator 19 and in the lead 15b to the voltmeter 22, it is not necessary to hold switch 18 in the position shown in FIG. 5 when a measurement is to be taken and also resistance 27 should then be omitted.

Where cathodic protection is insignificant and/or the current i is not continuously passed through the elements but is only applied at intervals when a measurement of resistance is to be taken, reversing switch 18, resistance 27, and switch 23 can be omitted. Where the current i is applied only at intervals when a measurement is to be taken, an on-off switch can be inserted in series with the test and reference elements 7a, 7b. However we prefer to maintain a current flowing through the elements to eliminate errors caused by varying thermoelectric voltages produced as the apparatus warms up to its equilibrium state.

Where a check element is connected in parallel with the test element as described below, cathodic protection and polarity reversal can be avoided, yet the equipment maintained at its equilibrium temperature by maintaining the current through the check element and only switching it to flow through the test element when a measurement is required.

Depending on the type of voltmeter used, switch 23 may be omitted in some cases, even where polarity reversal is employed.

Where a check element 7c is employed, the circuit modification of FIG. 6 may be used. Here the check element 7c is connected in parallel with the test element 7a using a two-pole two-way switch 28 having one pole interposed between the reversing switch 18 (if used) and the elements 7a, 7c and switching between the current application leads 14a, 14c, and the other pole interposed in the voltage feed-back line to voltage comparator 19 and switching between the voltage feed-back leads 15a, 15c.

To avoid errors resulting from thermoelectric effects, even when the current to the elements is maintained, the equipment shown within the dotted lines in FIGS. 5 and 6 is preferably maintained at a constant temperature e.g. by mounting in a thermostated enclosure.

The leads 13, 14, 15 to the elements 7 are preferably enclosed within an earthed screened cable 29. To avoid errors resulting from the resistances of the leads, the leads 14a, 14b used to supply the current to the elements are separate from the leads 15a, 15b used, with lead 13, to feed the voltage drops across the elements to the voltage comparator 19 and to voltmeter 22.

Where the elements 7a, 7b are not connected directly together but are connected by a further lead, whose resistance is not negligible in comparison with the resistance of the elements, lead 13 should be duplicated: one lead 13 being connected to element 7a and to the potential divider associated with the voltage standard 20, while the duplicate lead 13 being connected to the element 7b and to switch 24 and to the biasing voltage standard 25.

While it is not strictly necessary to use separate leads 14c, 15c for the check element 7c where one is connected in parallel with test element 7a, as described above, as the check element is only used to indicate the correct functioning of the equipment, the use of such separate leads 14c, 15c is preferred. If the check element 7c is made to have a resistance equal to that of the test element 7a, when the latter is in the uncorroded state, the check element can also be used to check the correctness of the zero adjustment on the voltmeter 22 effected by adjustment of resistance 26.

Providing the input impedances to the voltmeter 22 and, voltage comparator 19 are very high in comparison to the resistances of the elements 7 and the leads 13, 15, the effects of the resistances of leads 13, 15 can be neglected.

The apparatus is of primary utility in the continuing assessment of corrosion, including corrosion under heat transfer conditions, in pipes and vessels in e.g. oil installations and chemical plant. It may also be employed for laboratory assessment of corrosion occuring under heat transfer conditions. Such corrosion is often more severe and may be of a different nature to normal environmental corrosion. In order to simulate heat transfer conditions the test element, preferably together with the reference element, may be used as heating elements by passing a suitable electric current, preferably alternating current, therethrough during periods between corrosion measurements.

We claim:

1. A method of monitoring corrosion of the surface of a component subject to a corrosive environment comprising
    (i) forming an elongated strip test element from the material of said component,
    (ii) mounting said test element, out of contact with said component, in a surface in a housing so that one elongated surface of said test element and said surface of the housing are flush with said component surface, and are exposed to said corrosive environment, said one surface of the test element extending, in the direct of its length over substantially all of one dimension of said component surface, and (iii) monitoring the thickness of said test element.

2. A method according to claim 1 in which the strip test element is machined from a sample of the component.

3. A method according to claim 1 in which the thickness of the test element is monitored by comparing the thickness of the test element with that of a reference element mounted adjacent to the test element but protected from exposure to the corrosive environment.

4. A method according to claim 1 in which the test element is formed from an electrically conductive material and the thickness of the test element is monitored by monitoring the electrical resistance of the test element.

5. A probe for use in monitoring corrosion of the surface of a component subject to a corrosive environment comprising (i) a housing adapted for connection in-line with said component with the surface of said housing exposed to the corrosive environment flush with said surface of the component, and (ii) an elongated strip test element, formed from the material of said component, mounted in said housing so that the test element is out of contact with the component with one elongated surface of said element flush with said surface of the housing, exposed to the corrosive environment, and extending in the direction of its length over substantially all of one dimension of said component surface.

6. A probe according to claim 5 wherein the test element is located in a recess in the housing and an elongated strip reference element is located in said recess between the test element and the bottom of said recess, and said reference element is protected from exposure to the corrosive environment.

7. A probe according to claim 6 wherein an elongated strip check element is located in the recess between the test element and the bottom of the recess.

8. A probe according to claim 6 wherein the elements are electrically conductive and insulant material is interposed between the elements and, where the housing is electrically conductive, between the elements and the housing.

9. A probe according to claim 8 wherein the test and reference elements are connected in series and leads are provided whereby an electric current may be passed through the test and reference elements in series and the potential differences across the elements may be compared, one lead being connected to the connected ends of the test and reference elements, two leads being connected to the free end of the test element, and two leads being connected to the free end of the reference element.

10. A probe according to claim 5 wherein the component surface is the interior surface of a pipe, the housing is annular having an internal diameter equal to that of the pipe, and the exposed surface of the test element extends substantially all round the interior circumference of the housing.

11. Apparatus for monitoring corrosion of the surface of a component subject to a corrosive environment comprising a probe according to claim 5 in combination with means to monitor the thickness of the test element.

12. Apparatus according to claim 11 in which the probe is provided with an elongated strip reference element protected from exposure to the corrosive environment, said test and reference elements being electrically conductive and insulated from one another and from the housing, where the latter is electrically conductive except possibly at one point, said test and reference elements being connected in series, and said means to monitor the thickness of the test element comprises means to pass a current through the test and reference elements and to compare the potential difference across the reference element with that across the test element.

* * * * *